United States Patent
Kousaka et al.

(10) Patent No.: US 6,455,695 B1
(45) Date of Patent: Sep. 24, 2002

(54) PROCESS FOR THE PREPARATION OF ALKYLENEBISMELAMINES

(75) Inventors: Hiroyuki Kousaka; Yasuyuki Nakajima, both of Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 09/786,419

(22) PCT Filed: Sep. 3, 1999

(86) PCT No.: PCT/JP99/04782

§ 371 (c)(1),
(2), (4) Date: Mar. 6, 2001

(87) PCT Pub. No.: WO00/17171

PCT Pub. Date: Mar. 30, 2000

(30) Foreign Application Priority Data

Sep. 17, 1998 (JP) .......................................... 10-262643

(51) Int. Cl.⁷ ............................................. C07D 251/70
(52) U.S. Cl. ....................................................... 544/196
(58) Field of Search ......................................... 544/196

(56) References Cited

U.S. PATENT DOCUMENTS 4,136,092 A * 1/1979 Jackle et al. .................. 528/60
4,668,785 A 5/1987 Ebel et al. .................. 544/196
5,292,614 A 3/1994 Ochiai et al. ............... 430/270

FOREIGN PATENT DOCUMENTS

| DE | 3422218 A1 | 12/1985 |
| DE | 3611420 A1 | 10/1987 |
| EP | 0166297 A1 | 1/1986 |
| EP | 0240867 A1 | 10/1987 |
| JP | 61-10567 A | 1/1986 |
| JP | 5-224420 A | 9/1993 |

OTHER PUBLICATIONS

Kaiser et al., J. Am. Chem. Soc., vol. 73, pp 2984–2986 (1951).

* cited by examiner

*Primary Examiner*—Mukund J. Shah
*Assistant Examiner*—Venkataraman Balasubrasubramanian
(74) *Attorney, Agent, or Firm*—Oliff & Berridge, PLC

(57) ABSTRACT

The present invention provides a process which enables easy and inexpensive preparation of alkylenebismelamines usable as components for forming resin materials, particularly aminoplasts, and flame retardants. The present invention is a process for preparation of alkylenebismelamines wherein the alkylene is a linear or branched $C_{2-10}$ one by reacting an alkylenediamine wherein the alkylene is a linear or branched $C_{2-10}$ one with melamine in the presence of an acidic catalyst under heating, characterized in that the amount of melamine is at least twice that of the alkylenediamine by mole.

11 Claims, No Drawings

PROCESS FOR THE PREPARATION OF ALKYLENEBISMELAMINES

TECHNICAL FIELD

The present invention relates to a process for preparation of alkylenebismelamines.

BACKGROUND ART

Alkylenebismelamines are useful compounds which can be used as components for forming resin materials, particularly aminoplasts, and flame retardants. As reported in J. Am. Chem. Soc., Vol. 73, pages 2984–2986 (1951), the prior process for preparation of alkylenebismelamines has been carried out by reacting 2-chloro-4,6-diamino-1,3,5-triazine with an alkylenediamine. Although the prior process is excellent in obtaining several substituted melamines, the process has a problem that raw materials therefor are not inexpensive.

In addition, it is known to replace an amino group of melamine by several amines such as alkylamine, arylamine or the like in the presence of an acidic catalyst [the method mentioned above is described in the following documents: DE 3422218 A1 (1985) (corresponding patents: EP 0166297 A1 (1986), JP 61010567 A (1986), U.S. Pat. No. 4,668,785 A (1987)), DE 3611420 A1 (1987) (corresponding patent: EP 0240867 A1 (1987)) and so on].

DE 3611420 A1 (1987) discloses that 10 mol or more of alkylenediamines are made to react with 1 mol of melamine to produce tris(aminoalkyl)melamine as substituted melamine, and dimer of the substitutedmelamines. Further, the document discloses that when 1 to less than 10 mol of alkylenediamines are made to react with 1 mol of melamine, the amount of the resulting tris(aminoalkyl)melamine decreases compared with the case wherein 10 mol or more of alkylenediamines are used, and that the amount of the oligomer and polymer of the substituted melamines increases.

However, the document does not disclose that alkylenebismelamines produced by the process of the present invention can be obtained in single-step.

The present inventors have studied eagerly in order to solve the problems describe d above, and found the process of the present invention in which alkylenebismelamines can be produced in single-step by reaction between alkylenediamines and melamines in the presence of an acidic catalyst.

It is an object of the invention to provide a process which enables easy and inexpensive preparation of alkylenebismelamines usable as components for forming resin materials, particularly aminoplasts, and flame retardants.

DISCLOSURE OF INVENTION

The invention relates to a process for preparation of an alkylenebismelamine of formula (2)

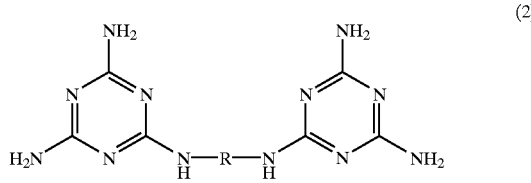
(2)

(wherein R is a linear or branched $C_{2-10}$ alkylene) by reacting an alkylenediamine of formula (1)

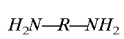
(1)

(wherein R is a linear or branched $C_{2-10}$ alkylene) with melamine in the presence of an acidic catalyst under heating, characterized in that the amount of melamine is at least twice that of the alkylenediarnine by mole.

R as a linear or branched $C_{2-10}$ alkyene is, for example, ethylene, 1,2- or 1,3-propylene, tetramethylene, pentamethylene, 2,2-dimethyltrimethylene, hexamethylene, heptamethylene, octarnethylene or decamethylene.

The reaction of the present process may be usually carried, out by adding at least 2 moles of melamine to 1 mole of alkylenediamine in the presence of an acidic catalyst under heating. About 2 to 10 moles, preferably about 2 to 5 moles of melamine is added to 1 mole of alkylenediamine.

Solvents used, in the present process may be any solvents as long as the solvents dissolve at least a little melamines and diamines, have the boiling point not less than 120° C., and do not participate in the reaction. The solvents are preferably alcohols such as ethylene glycol, diethylene glycol or the like.

Acidic catalysts used in the present process may be hydrochloric acid, hydrobromic acid, nitric acid, sulfuric acid, phosphoric acid, p-toluenesulfonic acid, methanesulfonic acid or the like. These acids may be added in the free form or in the form of melamine salt, amine salt or ammonium salt, etc. The amount of acidic catalyst to be added is 1 to 100 mole %, preferably 2 to 30 mole % based on melamine.

The reaction is usually carried out under heated conditions, for example at temperatures of 120 to 500° C., preferably at temperatures of 120 to 250° C. The reaction may be effected at atmospheric pressure, or effected in an autoclave. It is preferable to distill away ammonia gas generated in the course of the reaction by passing nitrogen gas into the reaction solution thereby to achieve a reduction in the reaction time and an improving in the yield. The reaction time can be determined by confirming the consumption of raw materials and the formation of aimed compounds. Generally, the reaction time may be 1 to 24 hours.

The post-treatment of the reaction and the collection of aimed compounds may be carried out in the usual way. Usually, crystals are crystallized by adding water to the reaction solution after optionally concentrating the solvent thereof, and then purification such as recrystallization may be attained as the occasion demands to collect aimed compounds. A mixture of aimed compounds and melamine can be adequately used for a certain purpose. The method of purification and the purity of aimed compound may be determined if necessary.

BEST MODE FOR CARRYING OUT THE INVENTION

The invention is further illustrated by Examples as follows, but the invention is not limited thereto.

EXAMPLE 1

Preparation of 1,6-Hexamethylenebismelamine

In a stainless steel autoclave having an inner volume of 70 ml, 6.3 g (0.05 mol) of melamine, 1.16 g (0.01 mol) of 1,6-hexanediamine (hexamethylenediamine), 0.27 g (0.005 mol) of ammonium chloride and 30.0 g of ethylene glycol are charged, and the atmosphere in the reactor is fully replaced with nitrogen gas. Under stirring, the temperature in the reactor is raised, and the reaction is carried out at 195° C. for 4 hours under passing through further nitrogen gas. The reaction solution is then cooled and 30ml of water is added thereto. Resulting white precipitate is separated off by filtration and washed with hot water to obtain 0.80 g (yield: 23.9%) of the object compound, 1,6-hexamethylenebismelamine.

EXAMPLE 2

Preparation of 1,2-Ethylenebismelamine

In a stainless steel autoclave having an inner volume of 70 ml, 6.3 g (0.05mol) of melamine, 1.20 g (0.02 mol) of ethylenediamine, 0.27 g (0.005 mol) of ammonium chloride and 30.0 g of ethylene glycol are charged, and the atmosphere in the reactor is fully replaced with nitrogen gas. Under stirring, the temperature in the reactor is raised, and the reaction is carried out at 195° C. for 4 hours under passing through further nitrogen gas. The reaction solution is then cooled and 30 ml of water is added thereto. Resulting white precipitate is separated off by filtration-land washed with hot water to obtain 0.80 g (yield: 14.5%) of the object compound, 1,2-ethylenebismelamine.

EXAMPLE 3

Preparation of 1,3-Propylenebismelamine

In a stainless steel autoclave having an inner volume of 70 ml, 6.3 g (0.05 mol) of melamine, 1.85 g (0.025 mol) of 1,3-propanediamine, 0.27 g (0.005 mol) of ammonium chloride and 30.0 g of ethylene glycol are charged, and the atmosphere in the reactor is fully replaced with nitrogen gas. Under stirring, the temperature of the reactor is raised, and the reaction is carried out at 195° C. for 4 hours under passing through further nitrogen gas. The reaction solution is then cooled and 30 ml of water is added thereto. Resulting white precipitate is separated off by filtration and washed with hot water to obtain 0.90 g (yield: 12.3%) of the object compound,1,3-propylenebismelamine.

EFFECT OF THE INVENTION

According to the method of the present invention, alkylenebismelamines that could not be directly synthesized from melamine in the prior can be directly produced from melamine in single-step following easy process for the preparation.

What is claimed is:

1. A process for preparation of an alkylenebismelamine of formula (2)

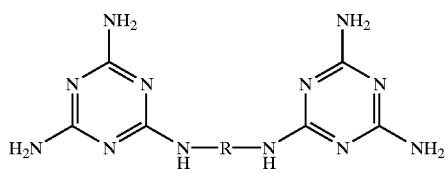

(wherein R is a linear or branched $C_{2-10}$ alkylene) by reacting an alkylenediamine of formula (1)

(wherein R is a linear or branched $C_{2-10}$ alkylene) with melamine in the presence of an acidic catalyst under heating, wherein the amount of melamine is at least twice that of the alklenediamine by mole.

2. The process for preparation according to claim 1, wherein the alkylenediamine of formula (1) is ethylenediamine, 1,3-diaminopropane or 1,6-diaminohexane.

3. The process for preparation according to claim 1, wherein the reaction is carried out in the presence of a solvent comprising ethylene glycol or diethylene glycol.

4. The process for preparation according to claim 1, wherein the reaction is carried out, at a temperature of 120 to 250° C.

5. The process for preparation according to claim 1, wherein the reaction is carried out under passing nitrogen gas.

6. The process for preparation according to claim 2, wherein the reaction is carried out in the presence of a solvent comprising ethylene glycol or diethylene glycol.

7. The process for preparation according to claim 2, wherein the reaction is carried out at a temperature of 120 to 250° C.

8. The process for preparation according to claim 2, wherein the reaction is carried out under passing nitrogen gas.

9. The process for preparation according to claim 3, wherein the reaction is carried out at a temperature of 120 to 250° C.

10. The process for preparation according to claim 3, wherein the reaction is carried out under passing nitrogen gas.

11. The process for preparation according to claim 4, wherein the reaction is carried out under passing nitrogen gas.

* * * * *